(12) United States Patent
Vavrick

(10) Patent No.: US 6,945,088 B2
(45) Date of Patent: Sep. 20, 2005

(54) MULTI-FRAGMENT IMPACT TEST SPECIMEN

(75) Inventor: Daniel J. Vavrick, Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 38 days.

(21) Appl. No.: 10/145,603

(22) Filed: May 14, 2002

(65) Prior Publication Data

US 2003/0213283 A1 Nov. 20, 2003

(51) Int. Cl.[7] .......................... G01L 25/00; G01L 5/00; G01L 5/24; G01M 19/00
(52) U.S. Cl. .................................... 73/11.01
(58) Field of Search .................. 73/11.01, 12.11, 73/167, 379.05; 102/387, 494, 213, 211, 363, 506, 520, 523; 435/6; 124/56; 701/41; 273/327; 482/110, 108

(56) References Cited

U.S. PATENT DOCUMENTS 3,648,610 A * 3/1972 Van Zyl et al. ............ 102/4
3,818,833 A * 6/1974 Throner, Jr. .............. 102/7.2
3,851,880 A * 12/1974 Ritch ..................... 273/128 R (Continued)

OTHER PUBLICATIONS

AE Aeragon—Chain Shot and Bar Shot, http://www.aeragon.com/o/am/a-03.html, Mar. 1, 2005, 2 pages.
HMS Victory Ordnance Charges & Ammunition, http://www.hms-victory.com/index2.php?option=content&task=view&id=33&pop=1&page=0, Mar. 1, 2005, 3 pages.

Primary Examiner—Max Noori
Assistant Examiner—Octavia Davis
(74) Attorney, Agent, or Firm—James B. Bechtel, Esq.; Marguerite O. Dineen, Esq.; Scott R. Boalick, Esq.

(57) ABSTRACT

A multiple fragment impact test specimen, and a method for using it in multiple fragment impact tests against a target, is disclosed. The test specimen comprises two or more fragments fixed to one or more connecting members so that the fragments are held at a fixed distance apart during their flight to a target. The orientation and speed of the fragments at the moment of impacting the target are measured and the measurements are used to calculate the exact spacing and time delay between the individual fragment impacts. An experimenter can control the range of fragment spacings and time delays for a series of tests by choosing the lengths of the connecting members and thereby fixing the relative distances between the fragments.

14 Claims, 2 Drawing Sheets

U.S. PATENT DOCUMENTS

| | | | |
|---|---|---|---|
| 4,036,141 A | 7/1977 | Korr et al. | 102/38 |
| 4,080,900 A | 3/1978 | Augenstein et al. | 102/67 |
| 4,102,271 A | 7/1978 | Bethmann | 102/52 |
| 4,155,308 A | 5/1979 | Murawski | 102/93 |
| 4,182,317 A * | 1/1980 | Ash | 128/28 |
| 4,216,722 A | 8/1980 | Angell | 102/91 |
| 4,242,960 A | 1/1981 | Boeder et al. | 102/92.7 |
| 4,362,107 A | 12/1982 | Romer et al. | 102/520 |
| 4,505,203 A * | 3/1985 | Brady et al. | 102/382 |
| 4,516,502 A | 5/1985 | Klein et al. | 102/523 |
| 4,517,899 A | 5/1985 | Haberli | 102/521 |
| H265 H | 5/1987 | Bonde et al. | |
| 4,662,280 A * | 5/1987 | Becker et al. | 102/364 |
| 4,695,051 A * | 9/1987 | Jenison | 272/122 |
| 4,696,182 A * | 9/1987 | Meir | 73/12 |
| 4,753,172 A | 6/1988 | Katzmann et al. | 102/517 |
| 4,785,800 A * | 11/1988 | Stilson | 128/57 |
| 4,796,883 A * | 1/1989 | Ratner | 482/109 |
| 4,830,364 A * | 5/1989 | Wexler | 272/93 |
| 4,939,997 A | 7/1990 | Hoffman | 102/503 |
| 4,947,755 A | 8/1990 | Burczynski | 102/506 |
| 5,014,931 A * | 5/1991 | Mikhail | 244/3.25 |
| 5,020,437 A | 6/1991 | Rieger et al. | 102/489 |
| 5,103,736 A | 4/1992 | Sowash | 102/523 |
| 5,111,746 A | 5/1992 | Pentel et al. | 102/308 |
| 5,250,014 A * | 10/1993 | Chang | 482/106 |
| 5,263,418 A | 11/1993 | Dippold et al. | 102/509 |
| 5,322,016 A * | 6/1994 | Toth | 102/211 |
| 5,454,325 A | 10/1995 | LeBlanc | 102/506 |
| 5,522,597 A * | 6/1996 | Hanks | 473/514 |
| 5,528,989 A | 6/1996 | Briese | 102/506 |
| 5,714,675 A * | 2/1998 | Yoshida et al. | 73/12.04 |
| 5,801,324 A | 9/1998 | Pickard | 102/516 |
| 6,010,580 A | 1/2000 | Dandliker et al. | 148/403 |
| 6,021,716 A | 2/2000 | Taylor | 102/517 |
| 6,109,185 A | 8/2000 | Mikhail | 102/476 |
| 6,186,071 B1 * | 2/2001 | Fry | 102/515 |
| 6,186,094 B1 | 2/2001 | Kamdar | 119/520 |

* cited by examiner

Spacing: $0 < (L+D)\cos\theta < (L+D)$
Time Delay: $0 < (L+D)\sin\theta/V < (L+D)/V$

MULTI-FRAGMENT IMPACT TEST SPECIMEN

STATEMENT REGARDING FEDERALLY SPONSORED RESEARCH OR DEVELOPMENT

The invention claimed and disclosed herein may be manufactured and used by, or on behalf of, the Government of the United States of America for government purposes without the payment of any royalties thereon or therefor.

REFERENCE TO A MICROFICHE APPENDIX

Not Applicable.

CROSS-REFERENCE TO RELATED APPLICATIONS

Not Applicable.

BACKGROUND OF THE INVENTION

1. Field of the Invention

This invention relates generally to armor and munitions test equipment and, more particularly, to test specimens for use in armor or explosive testing.

2. Description of the Related Art

It is known in the art to launch a variety of individual test specimens, or fragments, to impact an explosive target during, e.g., testing of explosive shells. These test specimens are typically placed into a specially adapted sabot which is launched from a launching device such as a gas or powder gun aimed toward the target. When the sabot clears the gun, aerodynamic forces cause the sabot to separate from the test specimen, thereby allowing the test specimen to proceed unimpeded toward the target.

In some instances, it is desirable to perform multiple-fragment tests to determine the effects of multiple fragments striking the target. In order to perform meaningful tests to determine the synergism effects on detonation or penetration of a target by multiple fragments, it is necessary to have some control over the distance between the fragments at the moment of impact as well as the time delay between impacts. Previous tests have been performed using separate, individual fragments accelerated in a sabot. However, using this method, it is not possible for the experimenter to control or vary the spacing of the fragments and the time delay between fragment impacts. If the fragments were fired from separate guns, the experimenter could control the spacing of the fragments. However, the time delay between the fragment impacts could not be controlled because it is not possible to synchronize the firing of two (or more) separate guns within sufficient tolerances to make the tests meaningful. For example, time delays of less than 20 microseconds are of interest in some tests.

SUMMARY OF THE INVENTION

The present invention provides a suitable test specimen and methods for constructing and using it when necessary to perform multiple fragment impact tests. Specifically, it allows an experimenter to control the spacing and time delay between fragment impacts by maintaining the fragments at a fixed distance apart during launch and flight toward the target. The test specimen comprises two or more fragments fixed to the ends of a connecting member to form a single, integrated unit. The fragments are preferably spherical to reduce the possibility of edge effects on the target. They can be affixed to the connecting members by a variety of methods, including gluing, welding, or through the use of threaded fittings. The preferred connecting member is a thin, rigid rod constructed from a stiff and strong material such as steel so that it will withstand the high g-forces associated with launch from a launching device without experiencing plastic deformation.

After the test specimen is constructed, it is placed in a sabot adapted to receive the test specimen and support it during launch so as to prevent plastic deformation. When shot from a launching device, the sabot separates from the test specimen and the test specimen continues unimpeded toward the target. The fragments strike the target within a range of fragment spacings and time delays controlled by the length of the connecting member. The actual fragment spacing and time delay between fragment impacts can easily be determined mathematically using the velocity and orientation of the test specimen at the moment of impact. The velocity and orientation of the fragments can be determined from, e.g., high speed photography or multiple x-rays.

BRIEF DESCRIPTION OF THE DRAWINGS

These and other features, aspects and advantages of the present invention will become better understood with regard to the following description, appended claims and accompanying drawings where:

DETAILED DESCRIPTION OF THE INVENTION

Figure 1:
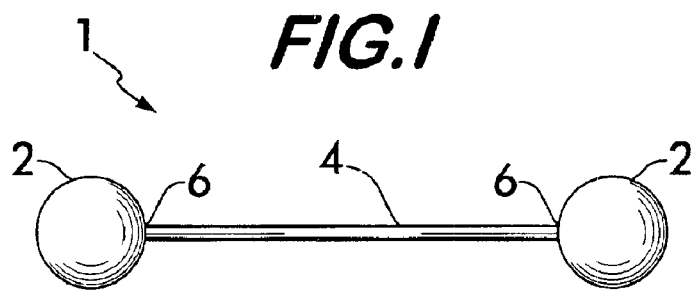
FIG. 1 shows a plan view of the preferred embodiment of the present invention.

FIG. 1 shows a test specimen 1 having two fragments 2 connected by a connecting member 4. The connecting member 4 has two ends 6. The preferred connecting member 4 is substantially cylindrical in shape and is constructed of a strong, rigid material, such as steel, that can withstand the g-forces associated with launch from a launching device without experiencing plastic deformation. The minimum strength of the connecting member material will be governed by the characteristics and weight of the test specimen 1, the acceleration of the test specimen during launch, and the support provided to the test specimen by the sabot in which it is launched. A fragment 2 is disposed on each end 6 of the connecting member 4. The fragments 2 are preferably spherical in shape, but other shapes may be employed to suit the requirements of the experimenter. For example, aerodynamic shapes may be employed to better control or predict the flight characteristics of the test specimen 1 during its flight to the target. A typical fragment 2 would be constructed of steel, however, any material chosen by the experimenter will work.

Figure 3:
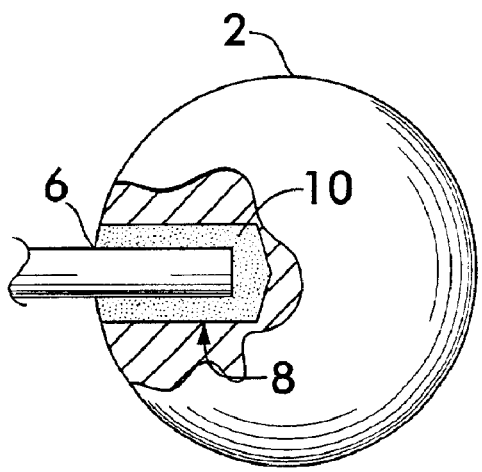
FIG. 3 shows a detail view of the attachment of a fragment to a connecting member end in accordance with the preferred embodiment of the invention.
Figure 4:
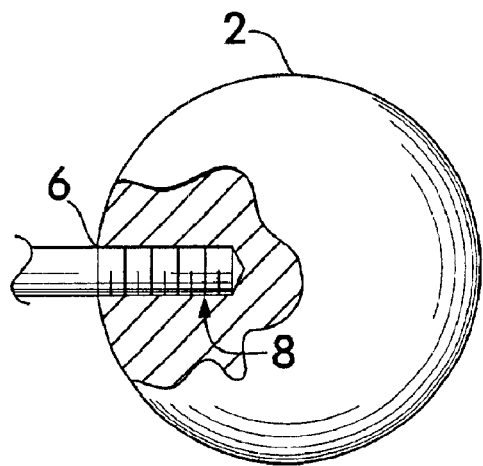
FIG. 4 shows a detail view of an alternative attachment of a fragment to a connecting member end.

The fragments 2 can be attached to the connecting member 4 by any method known in the art. In the preferred embodiment, the fragments 2 are glued to the connecting member ends 6 as shown in FIG. 3. A hole 8, having an inside diameter substantially equal to or greater than the diameter of an end 6, is machined into the fragment 2. An adhesive 10 is applied to the hole 8 and/or the end 6, and the end 6 is inserted into the hole 8. Another alternative is to screw the connecting member end 6 into hole 8 as shown in FIG. 4. In this embodiment, screw threads are machined into hole 8 and end 6 so that they can be joined together without the use of an adhesive. Yet another alternative is to weld the fragments 2 to the connecting member ends 6.

Figure 2:
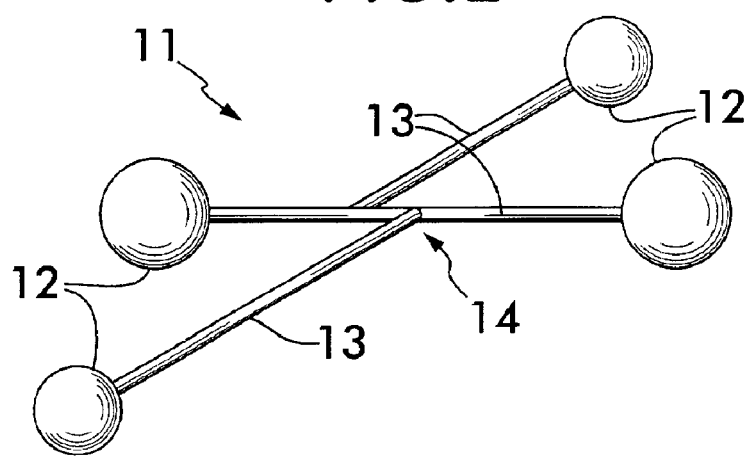
FIG. 2 shows a plan view of an alternative embodiment of the present invention having a connecting member with multiple arms.

So far, this description has focused on the preferred embodiment of the invention, having two fragments 2 and a connecting member 4 with two ends 6. However, a connecting member 14 having multiple arms 13, to which three or more fragments 12 can be connected, is possible as shown in FIG. 2. FIG. 2 shows a test specimen 11 having a connecting member 14 with three arms 13 and four fragments 12 connected to the ends of the arms. The only constraint on the size of a test specimen and the quantity of, and spacing between, its fragments is the maximum internal dimensions of the largest sabot that will fit in the launching device's barrel.

Figure 5:
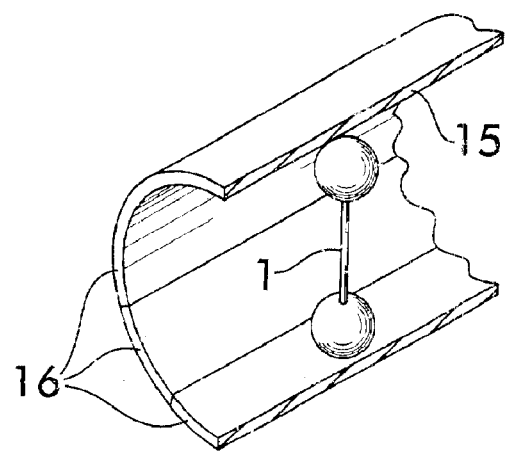
FIG. 5 shows a cut-away view of a test specimen loaded transversely into a sabot.
Figure 6:
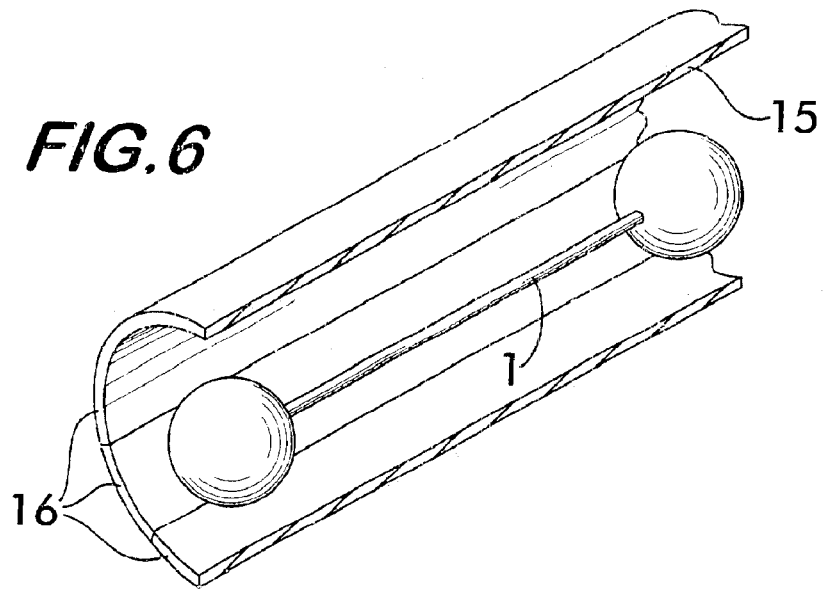
FIG. 6 shows a cut-away view of a test specimen loaded longitudinally into a sabot.

In operation, test specimen 1 is loaded into a sabot 15, wherein sabot 15 is specially adapted to support test specimen 1 as shown in FIGS. 5 and 6. Sabot 15 is illustrated in cross section so as to preferably disclose the orientation of test specimen 1 inside sabot 15. However, sabot 15 is completely cylindrical and consists of several sections 16 that will automatically separate after sabot 15 is launched from the launching device with minimal effect on test specimen's 1 orientation during its flight to the target. Sabot 15 is designed to support connecting member 4 and fragments 2 during launch from the launching device so that they do not sustain any plastic deformation induced by the launching g-forces. Methods for creating custom sabots to accommodate a variety of projectiles are currently known in the art. If the fragment spacing is small or the barrel diameter of the launching device is large, test specimen 1 may be installed in sabot 15 so that it lies perpendicular to the sabot's longitudinal axis as shown in FIG. 5. Otherwise, test specimen 1 is installed so that it lies parallel to the sabot's 15 longitudinal axis as shown in FIG. 6.

Figure 7:
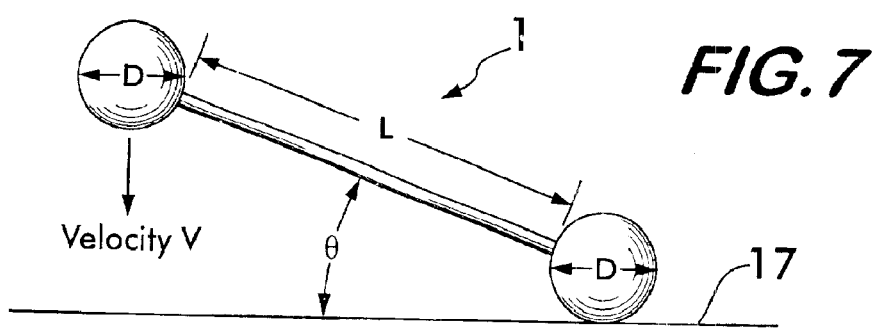
FIG. 7 shows a plan view of a test specimen impacting a target.

After test specimen 1 is loaded into sabot 15, sabot 15 is loaded into a launching device such as a gas or powder gun. The launching device is aimed at the target, such as a test section of explosive material covered by armor plating, and triggered. When sabot 15 exits the barrel of the firing device, its sections 16 are separated by aerodynamic forces, thereby freeing test specimen 1 to continue its flight unimpeded toward the target, subject to aerodynamic and inertial forces. After test specimen 1 is launched and released from sabot 15, it will fly as a tumbling rigid body with fragments 2 held at a fixed distance apart by connecting member 4. As shown in FIG. 7, test specimen 1 strikes target 17 at a velocity V and orientation θ that can readily be measured using methods known in the art. For example, multiple x-rays or high speed photographs may be employed to show the experimenter the orientation of test specimen 1 at, or very near, the moment of its impact on target 17.

The formulas shown in FIG. 7 may be used to calculate the actual spacing and time delay of fragments 2 when they impact target 16. Even though the orientation (angle) of test specimen 1 at the moment of impact cannot be controlled, the fixed relative spacing between the fragments 2 in test specimen 1 will allow the experimenter to control the range of spacings and time delays between fragment impacts for each series of tests using the formulas shown in FIG. 7 as guidance. A person skilled in the art of armor and munitions testing can readily expand the formulas shown in FIG. 7 to calculate the range of fragment spacings and time delays for a test specimen having more than two fragments, such as the test specimen 11 shown in FIG. 2.

While the above discussion describes the preferred embodiment of the invention and some alternative embodiments, it should be understood that they have been presented by way of example and not limitation. It will become apparent to those skilled in the art that equivalent alternative embodiments and alternative methods are possible. It is intended that all such alternative embodiments and methods shall be covered by the claims set forth herein.

What is claimed is:

1. A test specimen suitable for multiple-fragment impact tests against a target, comprising:
   at least two three-dimensional fragments suitable for launching at and impacting a target;
   a rigid connecting member having a plurality of ends, with one of said fragments coupled to each of said ends so that said connecting member thereby maintains said fragments at a fixed distance apart when they are launched at the target; and
   a separable sabot configured to support said fragments and said connecting member during launch from a launching device so that said fragments and said connecting member do not sustain plastic deformation induced by launching g-forces.

2. The test specimen of claim 1, wherein said fragments are coupled to said ends by an opening formed in each of said fragments suitable for fixedly receiving said ends.

3. The test specimen of claim 2, wherein said ends are fixed in said openings by adhesive.

4. The test specimen of claim 2, wherein said ends and said openings are threaded so that said ends are fixed into said openings by threading said ends into said openings.

5. The test specimen of claim 1, wherein said fragments are coupled to said ends by welding said fragments to said ends.

6. The test specimen of claim 1, wherein said connecting member comprises at least one cylindrical arm suitable for resisting deformation when said connecting member and said fragments are subjected to high g-force loadings as they are accelerated toward said target.

7. The test specimen of claim 1, wherein said fragments are substantially spherical.

8. The test specimen of claim 1, wherein said fragments are constructed of steel.

9. A test specimen suitable for multiple-fragment impact tests against a target, comprising:
   a rigid connecting member having a first end, a second end, and a third end;
   a spherical first fragment fixedly disposed on said first end of said connecting member;
   a spherical second fragment fixedly disposed on said second end of said connecting member;
   a spherical third fragment fixedly disposed on said third end of said connecting member so that said third fragment is maintained at a fixed distance from said first fragment and said second fragment when they are launched at a target; and
   a separable sabot configured to support said fragments and said connecting member during launch from a launching device.

10. The test specimen of claim 1 wherein said sabot is cylindrical.

11. The test specimen of claim 10 wherein said fragments and said connecting member are oriented perpendicular to a longitudinal axis of said sabot.

12. The test specimen of claim 10 wherein said fragments and said connecting member are oriented parallel to a longitudinal axis of said sabot.

13. The test specimen of claim 9 wherein said third fragment is not collinear with said first fragment and said second fragment.

14. The test specimen of claim 9 wherein:

said connecting member further comprises a fourth end; and said test specimen further comprises a fourth fragment fixedly disposed on said fourth end of said connecting member so that said fourth fragment is maintained at a fixed distance from said first fragment, said second fragment, and said third fragment when they are launched at a target.

* * * * *